United States Patent [19]

Eckert et al.

[11] 4,202,888

[45] May 13, 1980

[54] READILY ENTERALLY ABSORBABLE PHARMACEUTICAL COMPOSITIONS OF CARDIAC GLYCOSIDES AND PREPARATION THEREOF

[75] Inventors: Theodor Eckert; Fritz H. Kemper, both of Muenster; Martin Wischniewski, Neustadt a. Rbge.; Reinhard Hempel, Hanover, all of Fed. Rep. of Germany

[73] Assignee: Kali-Chemie Pharma GmbH., Hanover, Fed. Rep. of Germany

[21] Appl. No.: 813,456

[22] Filed: Jul. 7, 1977

[30] Foreign Application Priority Data

Jul. 12, 1976 [DE] Fed. Rep. of Germany ....... 2631214
Nov. 18, 1976 [DE] Fed. Rep. of Germany ....... 2652508
Dec. 1, 1976 [DE] Fed. Rep. of Germany ....... 2654386
Dec. 3, 1976 [DE] Fed. Rep. of Germany ....... 2654844

[51] Int. Cl.² .................. A61K 31/705; C07J 17/00
[52] U.S. Cl. ............................ 424/182; 536/5; 536/6; 536/7
[58] Field of Search ............ 424/182, 312; 536/5, 536/7

[56] References Cited

U.S. PATENT DOCUMENTS

| | | | |
|---|---|---|---|
| 3,458,628 | 7/1969 | Kaiser et al. | 536/7 |
| 3,462,528 | 8/1969 | Voigtlander et al. | 424/182 |
| 3,514,441 | 5/1970 | Satoh et al. | 536/7 |
| 3,910,881 | 10/1975 | Scheller et al. | 536/7 |
| 3,915,957 | 10/1975 | Kaiser et al. | 536/7 |
| 3,947,404 | 3/1976 | Kaiser et al. | 536/7 |
| 3,966,918 | 6/1976 | Kawamata et al. | 536/5 |
| 4,031,303 | 6/1977 | Murai et al. | 536/5 |

FOREIGN PATENT DOCUMENTS

1432784 4/1976 United Kingdom .............. 424/312

Primary Examiner—Johnnie R. Brown
Attorney, Agent, or Firm—Schwartz, Jeffery, Schwaab, Mack, Blumenthal & Koch

[57] ABSTRACT

A readily enterally absorbable pharmaceutical composition of cardiac glycosides is disclosed which comprises a therapeutically-effective amount of at least one cardiac glycoside distributed in a vehicle comprising an absorption-enhancing amount of at least one partial glyceride of a fatty acid of medium chain length. The preparation is suited for formulating cardiac glycosides which per se are poorly enterally absorbable, in particular, k-strophanthin, g-strophanthin, and proscillaridin.

12 Claims, No Drawings

READILY ENTERALLY ABSORBABLE PHARMACEUTICAL COMPOSITIONS OF CARDIAC GLYCOSIDES AND PREPARATION THEREOF

BACKGROUND OF THE INVENTION

The present invention relates to readily absorbable enteral pharmaceutical formulations of cardiac glycosides, which are poorly absorbable per se, and to a method for preparing such formulations.

Because of their favorable effect on the force of the myocardial contraction, cardiac glycosides are used therapeutically as cardiotonics for the treatment of myocardial insufficiency and congestive heart failure. Yet such a treatment has the disadvantage that upon enteral application, most of the cardiac glycosides are absorbed only to a low and unpredictable percent and thus, a safe therapy can often be achieved only by intravenous injection. Therefore, various attempts have been made to bring cardiac glycosides into a form which is suitable for enteral application.

Chemical derivations of such glycosides have been successful to a certain degree in some cases, e.g., digitoxin or digoxin, which are absorbable completely or to at least an acceptable degree, respectively. Yet other cardiac glycosides, such as, e.g., g- and k-strophanthin and proscillaridin still have to be administered parenterally, that is, intravenously, because of their insufficient enteral absorbability.

For several pharmacologically active agents, it has been proposed to dissolve or suspend them in glycerides of fatty acids having a medium chain length in order to improve their absorption. Thus, for example, according to German Pat. No. 1,282,853, chloramphenicol is suspended in triglycerides of fatty acids having a medium chain length. Belgian Pat. No. 567,598 discloses a suspension of antibiotics in triglycerides. British Pat. No. 1,432,784 discloses a solution or suspension of various pharmacologically-active agents in monoglycerides and German Offenlegungsschrift No. 2,357,389 discloses the solution or suspension of the same agents in a mixture of triglycerides and partial glycerides. Yet insofar as any data relative to the achieved absorption are included in the above references, these data indicate only little improvement of the absorption of the respective pharmacologically-active ingredients.

SUMMARY OF THE INVENTION

It is an object of the present invention to provide an enteral pharmaceutical formulation of cardiac glycosides, especially cardiac glycosides, which per se are poorly absorbable, which provide for a high degree of enteral absorption of such glycosides.

It is a further object of the present invention to provide such a formulation wherein the enteral absorption of poorly absorbable cardiac glycosides, especially of g-strophanthin, k-strophanthin and proscillaridin is increased sufficiently to permit an enteral application of these glycosides.

It is still a further object of the present invention to provide such a formulation wherein the enteral absorption of poorly absorbable cardiac glycosides is sufficiently high to insure a constant degree of absorption of such glycosides after enteral application.

In order to accomplish the foregoing objects and advantages of the present invention, there is provided a readily absorbable pharmaceutical composition which comprises a therapeutically-effective amount of at least one cardiac glycoside distributed in a vehicle comprising an absorption enhancing amount of at least one partial glyceride of a fatty acid of medium chain length.

The cardiac glycoside may be incorporated in the partial glyceride or a mixture of partial glycerides, respectively, in form of a genuine solution, a solid solution or a microcrystalline suspension.

The preparation according to the present invention is preferably suited for formulating cardiac glycosides which per se are poorly enterally absorbable, in particular, k-strophanthin, g-strophanthin and proscillaridin.

According to the present invention, there is further provided a process for preparing a readily enterally absorbable pharmaceutical composition of cardiac glycosides which comprises the step of dissolving the cardiac glycosides in at least one partial glyceride of a fatty acid of medium chain length.

According to the present invention, there is further provided a method of enteral cardiotonic therapy, which comprises enterally, preferably orally, administering the above described pharmaceutical composition to a larger mammal.

DETAILED DESCRIPTION OF PREFERRED EMBODIMENTS

According to the actual absorption data which are given in some of the above-cited prior art references, the achieved improvement of the absorption of the respective active agents is so little that it could not be expected that dissolving or suspending cardiac glycosides in partial glycerides of fatty acids of medium chain length leads to a useful and satisfactory increase of the enteral absorption of such glycosides. Cardiac glycosides exhibit a low therapeutic ratio, that is, the ratio between the therapeutically-effective and the toxic amount, combined with a large range of variations between the individual degrees of enteral absorption in different persons. The low therapeutic ratio indicates the fact that such agents have no effect at a dosage only slightly below the effective amount but lead to a perisystole at only a slight overdosage. Thus, due to a difference in the individual enteral absorption, an enteral dosage which has no effect in one individual may already cause the death of another individual. For example, with g-strophanthin, individual variations in enteral absorption in the range of between about 0.46% and 4.4%, that is, of a factor of 10, have been observed. Due to this, several authors have published their opinion that an enteral application of these glycosides cannot be effected. Because of such large individual variations of the degree of enteral absorption of poorly absorbable cardiac glycosides, a very high increase of the absorption has to be achieved in order to sufficiently equalize these individual differences to insure a safe enteral administration of the glycosides. In view of the only very small improvement of the absorption which was achievable by means of glycerides for other pharmacologically-active agents, it is highly surprising and unexpected that such a sufficiently large improvement of the enteral absorption of per se poorly absorbable cardiac glycosides is achieved according to the present invention.

The term cardiac glycosides, as it is used in the present application, includes cardiotonically-active glycosides containing a cardenolid- or bufadienolid aglycon, which is substituted in the 3-position by a glycosidic group containing 1 to 4 sugar units, and semi-synthetical derivatives thereof. The sugar units may be pentose or hexose units or partial reduction products thereof.

Cardiotonically-active semi-synthetic derivatives of naturally-occurring cardiac glycosides include the aglycones themselves, glycosides wherein the original number of sugar units is reduced, glycosides wherein the glycosidic group and/or the aglycon are chemically modified by etherification or esterification of at least part of the hydroxy groups with lower alkyl or lower carboxylic acyl, hydroxylation or dehydrogenation.

Among the cardiac glycosides with cardenolid structure, there may be cited the digitalis glycosides which occur naturally in digitalis purpurea and digitalis lanata, and derivatives thereof, e.g., lanatosids A, B or C, purpurea glycosides A or B, digitoxin, digoxin or gitoxin or the aglycons thereof, k-strophanthus glycosides which occur naturally in strophanthus kombe, g-strophanthus glycosides which occur naturally in strophanthus gratus, e.g., k-strophanthins $\alpha, \beta$ and $\gamma$ containing the aglycon k-strophanthidin (=$3\beta,5,14$-trihydroxy-19-oxo-$5\beta$-card-20(22)-enolid) and g-strophanthin containing the aglycon g-strophanthidin (=$1\beta,3\beta,5,11\alpha,14,19$-hexahydro-$5\beta$-card-20(22)-enolid).

Among the cardiac glycosides with bufadienolid structures, there may be cited the squill glycosides which occur naturally in scilla martima, e.g., proscillaridin scillaren A, scillaren B.

Preparations according to the present invention are especially suited for the enteral application of such cardiac glycosides which per se are particularly poorly enterally absorbable, for example, cardiac glycosides of which only about 5% or less, e.g., between about 5 and 0.3% are enterally absorbed. Examples of per se poorly enterally absorbable cardiac glycosides are g-strophanthin, k-strophanthin and proscillaridin. Preparations according to the present invention are also suited for the enteral application of cardiac glycosides for which it is desirable to improve their enteral absorption.

The concentration of the cardiac glycoside in the enteral preparations according to the present invention may vary considerably depending on the physical and chemical properties, especially the pharmacological activity of the respective cardiac glycoside which is used, on its enteral absorbability per se, and on its sensitivity to metabolic decomposition in the gastrointestinal tract and/or the liver, as well as on the amount of absorption enhancing partial glycerides present in the preparation and the contemplated mode of administration, the treated condition and the therapy which is desired. Usually a satisfactory enteral activity is obtained with an amount corresponding to between about 1 and about 3 times, preferably about 1 and about 2 times the parenterally-effective amount of the respective cardiac glycosides. For example, enterally-effective amounts of g-strophanthin, k-strophanthin or proscillaridin within the compositions according to the present invention are between about 0.1 and about 0.3, preferably about 0.2 and 0.25 mg per single dosage unit.

Partial glycosides of fatty acids of medium chain length comprise mono- and diglycerides of fatty acids, preferably saturated monocarboxylic acids, having a chain length of preferably between about 6 to about 12, most preferably between about 8 and about 10 carbon atoms, and mixtures thereof. Especially suited are mono- and diglycerides of capric- and caprylic acid and mixtures thereof.

The amount of absorption enhancing partial glycerides of fatty acids of medium chain length in the preparation according to the present invention, which is effective to sufficiently enhance the enteral absorption to permit an enteral administration of a cardiac glycoside, may vary considerably depending on the per se enteral absorbability of the respective cardiac glycoside, as well as on the chemical and physical properties of any other ingredients of the composition. Typically, satisfactory results are obtained with preparations wherein the amount of partial glycerides of fatty acids of medium chain length are between about 20 and about 100%, preferably about 40 and about 100%, of the vehicle. For example, of oral preparations of cardiac glycosides the per se enteral absorbability of which is less than 5%, e.g., between 0.3 and 5%, such as g-strophanthin, k-strophanthin or proscillaridin, the partial glycerides of fatty acids of medium chain length are preferably used in amounts of about 40 to about 100% of the total vehicle.

The ratio between the amounts of cardiac glycoside and of absorption enhancing partial glycerides of fatty acids of medium chain length may vary considerably depending on the per se enteral absorbability of the respective cardiac glycoside, as well as on the chemical and physical properties of any other ingredients of the composition. For example, for enteral preparations of cardiac glycosides having a per se enteral absorbability of less than 5%, e.g., of between 0.3 and 5%, a suitable ratio cardiac glycoside/partial glyceride of fatty acids of medium chain length is of between about 0.5 to 100 and about 0.01 to 100.

The enteral formulations may take the form of solid or liquid formulations for oral or rectal application. Thus, the formulations may be in the form of capsules, tablets, coated tablets, suppositories or emulsions. These formulations may comprise conventional pharmaceutical carriers and additives, especially viscosity-improving and/or structure- or matrix-forming additives which provide for an appropriate viscosity and physical structure. Suitable such additives are, e.g., inorganic thickening agents, such as, highly dispersed silicic acid (e.g., the commercial products 37 Aerosil") bentonites, collodial clay, modified montmorillonites, such as alkyl ammonium salts of montmorillonites (e.g., the commercial products "Bentone") wherein the alkyl groups may contain 1 to 20 carbon atoms, e.g., dimethyldialkyl ammonium salts wherein the alkyl groups contain 16 to 18 carbon atoms, organic thickening and structure-forming agents such as, saturated higher fatty acids and alcohols containing, e.g., 12 to 20 carbon atoms, for example, stearic or palmitic acid, stearic or cetylic alcohol, waxes like beeswax, synthetic esters of higher fatty acids and higher fatty alcohols, or spermaceti, monoglycerides of saturated or unsaturated higher fatty acids, e.g., monoglycerides of stearic acid, palmitic acid or oleic acid, partial glycerides of fatty polyhydroxy acids (e.g., the commercial products "Softigen 701"). Suppositories may further contain any conventional water soluble or fatty suppository bases as additional vehicles. The compositions may further comprise pharmaceutical adjuvants, e.g., binders or lubricants for tabletting, stabilizing-, flavoring-, or emulsifying agents or preservatives.

Since several cardiac glycosides are sensitive to acids, it may be advisable to apply an enteric coating to the oral dosage forms, e.g., gelatin capsules, of such glycerides.

The formulations according to the present invention are prepared in any conventional manner, e.g., by dissolving the cardiac glycosides in the partial glycerides, optionally adding additional adjuvants, and formulating the resulting mixture into the desired dosage form by known pharmaceutical methods, e.g., tabletting, molding into suppositories or filling into capsules.

Depending on the solubility and/or the dissolution rate of the cardiac glycosides in the partial glycerides and on the melting point of the partial glycerides, the dissolving may be done at room temperature or under heating. In cases where the cardiac glycosides recrystallize and/or the partial glycerides resolidify upon cooling of such solutions which are obtained under heating, microcrystalline suspensions and/or solid solutions of the glycosides are formed, which exhibit the same absorption behavior as that of actual solutions of the cardiac glycosides.

In order to facilitate the filling of the mixture into gelatin capsules or the formulating into suppositories or tablets, it may be advisable to further add viscosity-improving or structure- or matrix-forming additives. Especially, there may be added highly dispersed silicic acid, modified montmorillonites, palmitic acid, stearic acid, cetylic or stearic alcohols, beeswax, or spermaceti.

The high enteral absorption of the formulations according to the present invention is demonstrated by toxicity tests, determination of the level of the respective glycosides in the blood or according to a modified Hatcher method as described by Lenke and Schneider (Arzneimittelforschung 19 (1969), pages 687–693; ibid 20 (1970), pages 1199–1206 and 1765–1770).

For testing the toxicity, solutions of g-strophanthin or proscillaridin in a mixture of mono- and diglycerides of capric and caprylic acids (commercial product of "Witafrol 7420", manufacturer Dynamit-Nobel AG) and in water are administered orally to female guinea pigs of 250 to 300 g body weight by means of an oral feeding tube. The following lethal doses are observed:

| Test solution | $LD_{50}$ mg/kg |
| --- | --- |
| g-strophanthin in Witafrol 7420 | 5.2 |
| g-strophanthin in water | 34.8 |
| Proscillaridin in Witafrol 7420 | 6.8 |
| proscillaridin in water | 12.3 |

For determining the blood level values, 50 µg/kg of tritiated g-strophanthin in form of solutions in a mixture of mono- and diglycerides of capric and caprylic acids (commercial product WL 2391, manufacturer Sa. Gattefosse) and in water are administered to cats intraduodenally. The measured blood level values are plotted on a graph and the area beneath the resulting blood level curves are compared. From the comparison of the areas, the following percentages of absorption are calculated:

g-strophanthin in water—19%
g-strophanthin in WL 2391—61%

According to the modified Hatcher-method ("fill up"-method) 100 µg/kg g-strophanthin dissolved in Witafrol 7420 is administered intraduodenally to cats of both sex which are under chloralose-urethane narcosis (at this dosage which normally is not lethal, two cats out of thirty-four died already). Four hours later, the active agent is "filled up" by means of intravenous infusion until perisystole occurs. The following statistical average absorption rates of between 60 and 80% are found depending on the predetermined period of survival.

| Intraduodenal administration | Predetermined period of survival (min) | Calculated (aver.) "fill up" dose of g-strophanthin µg/kg i.v. | enteral activity % |
| --- | --- | --- | --- |
| g-strophanthin 100 µg/kg in Witafrol | 50 | 63.9 | 80.8 |
| Witafrol | 100 | 49.7 | 60.7 |
| Witafrol | 50 | 144.7 | — |
| 0.1 ml/kg | 100 | 110.4 | — |

Due to the high enteral absorption rates of, e.g., up to 80%, which are achieved according to the present invention, a highly secure oral or rectal therapy, e.g., of myocardial insufficiency, with per se poorly absorbable cardiac glycosides, which could not be achieved heretofore, is made available.

The invention will now be further described by the following examples. In these examples, the term "parts" means "parts by weight" unless stated otherwise. The amount of a certain cardiac glycoside which is cited in one example can be replaced by the same amount of one of the other two cardiac glycosides which are cited in the examples.

EXAMPLE 1

Gelatin capsules:
Composition of the mixture which is filled into the capsules:

| | |
| --- | --- |
| g-strophanthin | 0.125 parts |
| mixture of mono- and diglycerides of capric and caprylic acid* | 99.875 parts |
| Total | 100.000 parts |

*commercial product WL 2391, manufacturer, Sa. Gattefosse

Preparation: g-strophanthin is dissolved in the glyceride mixture at a temperature of 35° to 40° C. under stirring. The solution is filled into gelatin capsules in portions of 200 mg per capsule. Each capsule contains 0.25 mg of the active ingredient.

EXAMPLE 2

Gelatin capsules:
Composition of the mixture which is filled into the capsules:

| | |
| --- | --- |
| g-strophanthin | 0.125 parts |
| mixture of mono- and diglycerides of capric and caprylic acids* | 92.375 parts |
| highly dispersed silicic acid containing an amount of $CH_3$ groups equivalent to a carbon content of 0.9–1.2%** | 7.500 parts |
| Total | 100.000 parts |

*commercial product WL 2391, manufacturer, Sa. Gattefosse
**commercial product Aerosil R 972, manufacturer Degussa Preparation: g-strophanthin is dissolved in the glyceride mixture at a temperature of 35° to 40° C. under agitation. Subsequently, the silicic acid is added under further agitation. For final homogenization, the mixture is treated in a colloid mill or a high pressure homogenizer. The mixture is filled into gelatin capsules in portions of 200 mg per capsule. Each capsule contains 0.25 mg of the active ingredient.

EXAMPLE 3

Composition of the mixture which is filled into the capsules:

| | |
|---|---|
| k-strophanthin | 0.125 parts |
| tetraalkyl ammonium salt of magnesium montmorillonite** | 4.5 parts |
| ethanol | 2.25 parts |
| mixture of mono- and diglycerides of capric and caprylic acids* | 93.125 parts |
| Total | 100.000 parts |

*commercial product WL 2391, manufacturer, Sa. Gattefosse
**commercial product of Bentone 27, manufacturer, Kronos Titan Preparation: the modified montmorillonite is added to about half the amount of the glyceride mixture and by means of a high speed agitator of the type Rotor/Stator. It is first dispersed therein and then subsequent to the addition of the ethanol, it is solubilized whereby a viscid gel is formed. The k-strophanthin is dissolved in the remaining amount of the glyceride mixture and the resulting solution is added to the previously prepared gel portion under agitation. Agitation is continued until a uniform consistency of the mixture is achieved. The mixture is filled into gelatin capsules in portions of 200 mg each. Each capsule contains 0.25 mg of active ingredient.

EXAMPLE 4

Composition of the mixture which is filled into the capsules:

| | |
|---|---|
| k-strophanthin | 0.125 parts |
| capric acid monoglyceride | 17.5 parts |
| mixture of mono- and diglycerides of capric and caprylic acid* | 82.375 parts |
| Total | 100.0 parts |

*commercial product Witafrol 7420, manufacturer, Dynamit-Nobel AG

Preparation: k-strophanthin is dissolved in the mixture of mono- and diglycerides of capric and caprylic acid at a temperature of about 35° to 40° C. under agitation. The capric acid monoglyceride is melted at a temperature of 60° C. and added to the above mixture, which is then allowed to cool to room temperature under agitation. Portions of 200 mg each of the mixture are filled into gelatin capsules, which subsequently are coated with an enteric coating. Each capsule contains 0.25 mg of active ingredient.

EXAMPLE 5

Gelatin capsules for rectal application

Composition of the mixture which is filled into the capsules:

| | |
|---|---|
| g-strophanthin | 0.025 parts |
| mixture of mono- and diglycerides of capric and caprylic acids* | 92.475 parts |
| highly dispersed silicic acid containing an amount of CH$_3$ groups equivalent to a carbon content of 0.9–1.2%** | 7.500 parts |
| Total | 100.000 parts |

*commercial product Witafrol 7420, manufacturer, Dynamit-Nobel AG
**commercial product Aerosil R 972, manufacturer Degussa Preparation: g-strophanthin is dissolved in the glycerides at a temperature of 35° to 40° C. under agitation. Subsequently, the silicic acid is added under further agitation. For the final homogenization of the mixture is treated in a colloid mill or a high pressure homogenizer. The mixture is filled into gelatin capsules for rectal application in portions of 1 g per capsule. Each capsule contains 0.25 mg of the active ingredient.

EXAMPLE 6

Suppositories

Composition:

| | |
|---|---|
| k-strophanthin | 0.01 parts |
| caprylic acid monoglyceride | 99.99 parts |
| Total | 100.00 parts |

Preparation: the caprylic acid monoglyceride (melting point 35°–37° C., purity 90%, remainder caprylic acid, diglyceride, and triglyceride and glycerine) is liquified at a temperature of 45° C. and the k-strophanthin is dissolved in the molten product under agitation. The molten mixture is filled into suppository molds wherein it solidifies. Each suppository weighs 2.5 g and contains 0.25 mg of k-strophanthin.

EXAMPLE 7

Suppositories

Composition:

| | |
|---|---|
| g-strophanthin | 0.01 parts |
| caprylic acid monoglyceride (purity 40%)** | 33.0 parts |
| suppository base*** | 66.99 parts |
| Total | 100.00 parts |

**commercial product Drewmulse GMC-8, manufacturer PVO International, Inc.
***commercial product Novata C, manufacturer, Henkel AG Preparation: g-strophanthin is dissolved in the caprylic acid monoglyceride at a temperature of 50° C. under agitation. The suppository base Novata C is also melted and added to the above mixture under agitation. The mixture is filled into suppository molds wherein it solidifies. Each suppository weighs 2.5 g and contains 0.25 mg of g-strophanthin.

EXAMPLE 8

One capsule which is prepared according to Example 1 is administered orally once a day to an adult person for cardiotonic therapy.

While the invention has now been described in terms of various preferred embodiment, the skilled artisan will readily appreciate that various substitutions, modifications, changes, and omissions may be made without departing from the spirit thereof. Accordingly, it is intended that the scope of the present invention be limited solely by that of the following claims.

What is claimed is:

1. A readily enterally absorbable pharmaceutical composition which comprises a therapeutically-effective amount of at least one cardiac glycoside selected from the group consisting of g-strophanthin, k-strophanthin and proscillaridin distributed in a substantially non-aqueous vehicle comprising an absorption-enhancing amount of at least one glyceride selected from the group consisting of mono-glycerides and diglycerides of fatty acids of medium chain length containing 6 to 12 carbon atoms and mixtures thereof.

2. The composition as defined in claim 1, which comprises a solution of the cardiac glycoside in the glyceride.

3. The composition as defined in claim 1, which comprises a microcrystalline suspension of the cardiac glycoside in the glyceride.

4. The composition as defined in claim 1, wherein the amount of the cardiac glycoside per single dosage unit is about 1 to about 2 times the parenterally-effective amount of the respective cardiac glycoside.

5. The composition as defined in claim 1, wherein the amount of the cardiac glycoside per single dosage unit is between about 0.1 and 0.3 mg.

6. The composition as defined in claim 1, wherein the fatty acids contain 8 to 10 carbon atoms.

7. The composition as defined in claim 1, which comprises a mixture of mono- and diglycerides of capric and caprylic acids.

8. The composition as defined in claim 1, wherein the amount of glycerides of fatty acids of medium chain length is between about 20 and about 100% by weight of the vehicle.

9. The composition as defined in claim 8, wherein the amount of the glycerides of fatty acids of medium chain length is from about 40 to about 100% by weight of the vehicle.

10. The composition as defined in claim 1, wherein the per weight ratio cardiac glycoside glyceride of fatty acids of medium chain length is of between about 0.5 to 100 and 0.01 to 100.

11. The composition as defined in claim 1, which further comprises pharmaceutical additives having viscosity-improving or structurizing properties selected from the group consisting of highly dispersed silicic acid, modified montmorillonites, oleic acid monoglyceride, stearic acid monoglyceride, palmitic acid, stearic acid, cetylic alcohol, stearylic alcohol, beeswax, spermaceti, and a mixture of mono- and diglycerides of an unsaturated hydroxy-substituted fatty acid.

12. A method of cardiotonic treatment which comprises enterally administering to a human being a readily enterally absorbable pharmaceutical composition which comprises a therapeutically-effective amount of at least one cardiac glycoside distributed in a vehicle comprising an absorption-enhancing amount of at least one glyceride selected from the group consisting of monoglycerides and diglycerides of fatty acids of medium chain length and mixtures thereof.

* * * * *